US010041864B2

(12) United States Patent
David (10) Patent No.: US 10,041,864 B2
(45) Date of Patent: Aug. 7, 2018

(54) AUTOMATIC RE-LOADING AIR-SAMPLING AND PNEUMATIC TRANSPORT SYSTEM

(71) Applicant: Brian J. David, Falls Church, VA (US)

(72) Inventor: Brian J. David, Falls Church, VA (US)

(*) Notice: Subject to any disclaimer, the term of this patent is extended or adjusted under 35 U.S.C. 154(b) by 299 days.

(21) Appl. No.: 15/098,405

(22) Filed: Apr. 14, 2016

(65) Prior Publication Data

US 2016/0231205 A1 Aug. 11, 2016

Related U.S. Application Data

(63) Continuation of application No. 14/466,132, filed on Aug. 22, 2014, now Pat. No. 9,341,547.

(Continued)

(51) Int. Cl.
*G01N 1/22* (2006.01)
*G01N 1/24* (2006.01)
(Continued)

(52) U.S. Cl.
CPC ............. *G01N 1/24* (2013.01); *G01N 1/2205* (2013.01); *G01N 1/2273* (2013.01);
(Continued)

(58) Field of Classification Search
CPC ............... G01N 1/2205; G01N 1/2214; G01N 2001/222; G01N 2001/2223; G01N 1/24
(Continued)

(56) References Cited

U.S. PATENT DOCUMENTS 4,869,117 A * 9/1989 McAndless .......... G01N 1/2214
73/863.21

5,691,487 A 11/1997 Green et al.
(Continued)

*Primary Examiner* — Robert R Raevis
(74) *Attorney, Agent, or Firm* — Clyde E. Findley (57) ABSTRACT

Embodiments of the invention collect solid, vapor, and/or biological components of the air in air-sampling cartridges that are then transported to an off-site location by pneumatic pressure. Operation proceeds by first collecting a sample of air in an air-sampling cartridge in a sampling position, then advancing a cartridge assembly to move the now-used sampling cartridge into a transport position while simultaneously moving an unused sampling cartridge into the sampling position, and finally using pneumatic pressure to push the used sampling cartridge in the transport position to an off-site location via a transport tube. The sampling operation can begin again while the transport operation is in still in progress. These operations can be pre-programmed locally or triggered by remote communication. Continued operation is possible due to a plurality of unused air-sampling cartridges retained in the cartridge assembly. Since operations can be triggered remotely and air samples are autonomously transported off site, embodiments of this invention eliminate unnecessary risks to human health created by other air-sampling devices, which require an operator to be present at a potentially hazardous sampling site to activate the device or retrieve air samples. Additionally, embodiments of the invention can be installed pre-emptively to eliminate risks to human health created when an operator must deliver a portable air-sampling device to a potentially contaminated sampling site. Furthermore, embodiments of the invention allow rapid retrieval of air samples following sample collection, which can expedite analysis and identification of aerosols and consequently help minimize human exposure to potentially dangerous and life-threatening chemical and biological contaminants.

14 Claims, 9 Drawing Sheets

Related U.S. Application Data

(60) Provisional application No. 61/959,659, filed on Aug. 29, 2013.

(51) Int. Cl.
 *G01N 33/00* (2006.01)
 *G01N 1/18* (2006.01)

(52) U.S. Cl.
 CPC ... *G01N 33/0036* (2013.01); *G01N 2001/185* (2013.01); *G01N 2001/2223* (2013.01)

(58) Field of Classification Search
 IPC ................................................... G01N 1/2205
 See application file for complete search history.

(56) References Cited

U.S. PATENT DOCUMENTS

| | | | |
|---|---|---|---|
| 6,167,767 B1 * | 1/2001 | Mengel | G01N 1/2273 73/863.01 |
| 8,978,491 B2 * | 3/2015 | Sinclair | G01N 9/02 73/863.41 |
| 2008/0304752 A1 | 12/2008 | Matteoni et al. | |
| 2009/0131818 A1 | 5/2009 | Speeg et al. | |
| 2014/0249451 A1 | 9/2014 | Mao et al. | |
| 2016/0054204 A1 | 2/2016 | David | |

* cited by examiner

AUTOMATIC RE-LOADING AIR-SAMPLING AND PNEUMATIC TRANSPORT SYSTEM

CROSS REFERENCE TO RELATED APPLICATIONS

This application is a continuation of U.S. patent application Ser. No. 14/466,132, filed Aug. 22, 2014, which claims priority under 35 U.S.C. § 119(e) to U.S. Provisional Patent Application Ser. No. 61/959,659, filed Aug. 29, 2013, which is hereby incorporated by reference.

BACKGROUND

The present invention is related to the field of air sampling. More particularly, the present invention is related to systems that automatically collect samples of air and transport those samples away from the sampling site during continued and uninterrupted operation.

DESCRIPTION OF RELATED ART

Systems that sample air for aerosols, including suspensions of solid or liquid particles, have been used in a wide range of applications. For example, systems have been used to sample and analyze vehicle exhaust, to ensure conformance with state pollution regulations. Systems have also been used to analyze the air surrounding suspected targets of biological warfare in order to identify hazardous airborne microorganisms, such as anthrax, and determine appropriate medical responses. The Environmental Protection Agency routinely samples air around the United States, not only to monitor atmospheric levels of ozone and carbon monoxide, but to also collect representative samples of airborne biological and radiological contaminants. Since aerosols are typically diffuse in the air, it is often necessary to first concentrate air samples on a sampling medium before analysis can be performed.

In order to concentrate aerosols, many air-sampling devices pull air through or over a filter, or other sampling medium, over a period of time. While some sampling media can selectively concentrate specific aerosols, other sampling media concentrate many aerosols collectively, to be separated and analyzed later. Some air-sampling devices can analyze collected samples autonomously, while others require the samples to be retrieved for off-site analysis at a laboratory. The utility of air-sampling devices that can analyze samples autonomously is often constrained by costly and delicate instrumentation needed for specialized analysis of the air samples. For example, coupling a gas chromatograph-mass spectrometer (GC-MS) to an air-sampling device would allow many aerosols to be identified at the molecular level, but would require a significant investment. GC-MS machines cost up to several hundred thousand dollars and may not be cost effective given the limited scope of analysis in the field. Furthermore, such a combination would require extensive calibration by a qualified technician prior to each use, to ensure accurate analysis, as transport alone could cause significant analytical variation in the results. A known example of such a system is the microfluidic bio-agent autonomous networked detector ("M-BAND") produced by PositiveID Corporation, which was at first considered for use in the Department of Homeland Security's BioWatch program, but recently abandoned due to high costs, frequent false positive results, and frequently required maintenance. A more practical and more cost-effective approach separates sample collection from analysis, but requires air samples to be retrieved from the sampling site and transported off-site to a laboratory.

All known air-sampling devices that collect and store air samples require an operator to retrieve air samples from the device at the sampling site. For example, the Portable Multi-Tube Air Sampler Unit disclosed in U.S. Pat. No. 8,196,479 encases multiple air sample-collection tubes into a portable container and requires an operator not only to deliver and activate the device at the sampling site, but also later to return in order to retrieve the entire unit, including the air samples contained within.

The Automatic Multi-Sorbent Tube Air Sampler ("AMTAS") disclosed in U.S. Pat. No. 6,477,906 can be installed at a sampling site to later collect air samples autonomously, but also requires an operator to retrieve the air samples whenever analysis is needed. Although the AMTAS is capable of allowing individual air samples to be removed during continued operation, the Portable Multi-Tube Air Sampler Unit and most other air-sampling devices require an operator to wait until the end of operation before the collected air samples can be retrieved.

Despite the benefits provided by the prior art systems, they nevertheless fall short of providing a system that eliminates the necessity for an operator to be present at the sampling site either for the retrieval of all air samples at the end of operation or for the retrieval of individual air samples during continued operation. Instead, prior art systems require a human operator to enter the sampling site wearing appropriate personal protective equipment (PPE) and risk contamination to install the device, activate collection, and retrieve air samples. Additionally, prior art systems fall short of providing a system where samples can be rapidly retrieved from an air-sampling system while allowing its continued concurrent sampling operation, and instead rely on a human operator to retrieve samples at the end of operation or to interrupt operation to retrieve samples prior to the end of operation.

SUMMARY

This Summary is provided to introduce certain concepts in a simplified form that are further described below in the Detailed Description. The Summary is not intended to identify key features or essential features of the claimed subject matter, nor is it intended in any way to limit the scope of the claimed invention.

Embodiments of the invention can sample aerosols by utilizing a vacuum pump to pull ambient air through an inlet tube and an aligned air-sampling cartridge, then subsequently align the cartridge with an outlet tube and transport it through the outlet tube to a remote destination using pneumatic pressure supplied by a compressor.

Embodiments of the invention can utilize air-sampling cartridges containing one or more sampling media designed to collect and concentrate a number of different aerosols. For example, an air-sampling cartridge containing fibrous, membranous, and/or perforated solid media can concentrate and collect solid airborne particulates whereas an air-sampling cartridge containing an adsorbent, such as activated charcoal, can concentrate and collect vapors. Embodiments of the invention can also utilize an air-sampling cartridge comprising a combination of two or more sampling media to collect combinations of aerosols simultaneously.

Embodiments of the invention have a "sampling position," which is a location between an inlet tube and a vacuum tube that can be occupied by any one of a plurality of chambers and where an air-sampling cartridge can collect aerosols from ambient air. Additionally, embodiments of the invention have a "transport position," which is a location between an outlet tube and a compressor line that can be occupied by any one of a plurality of chambers and where an air-sampling cartridge is subjected to pneumatic pressure to be transported away from the device in a transport tube.

Embodiments of the invention can arrange a plurality of chambers for retaining air-sampling cartridges in a circular pattern in a wheel assembly and can utilize a rotation mechanism, such as a Geneva drive, to rotate the wheel assembly and change the positions of the plurality of chambers. In such embodiments, the rotation mechanism can also hold the wheel assembly in position while an air sample is taken in an unused air-sampling cartridge at the sampling position while, at the same time, a used air-sampling cartridge at the transport position is subjected to pneumatic pressure and transported to a remote destination.

Alternatively, embodiments of the invention can arrange the plurality of chambers in a linear arrangement in a rectangular assembly and can utilize a translation mechanism, such as a piston or solenoid, to change the positions of the plurality of chambers. In such embodiments, the translation mechanism can also hold the rectangular assembly in position while an air sample is taken in an unused air-sampling cartridge at the sampling position and while a used air-sampling cartridge at the transport position is subjected to pneumatic pressure and transported to a remote destination.

Yet another embodiment of the invention can move an air-sampling cartridge from a storage compartment to a sampling position, and then subsequently to a transport position. In such an embodiment, the storage compartment and sampling position can be separated by a first gate, or other dividing mechanism, that creates a substantially airtight seal around the air-sampling cartridge in the sampling position. Additionally, the sampling position and transport position can be separated by a second gate, or other dividing mechanism, that creates a substantially airtight seal around the air-sampling cartridge in the transport position.

Embodiments of the invention can require manual loading of air-sampling cartridges into the plurality of chambers prior to operation, for example by using a hand-held push tool, while other embodiments of the invention can utilize a magazine of unused air-sampling cartridges and can load said unused cartridges into empty chambers by automated mechanical means known to those of ordinary skill in the art.

Embodiments of the invention can autonomously align a first one of the plurality of chambers retaining an air-sampling cartridge into the sampling position while simultaneously aligning a second one of the plurality of chambers into the transport position. Said autonomous rotation can be triggered by a pre-programmed set of instructions or on demand via remote communication. Said remote operation can be facilitated through wired or wireless communication any distance from the device, such as through a communications device directly interfaced with the system, or through a communications device connected to a local area network or intranet, or on a communications device anywhere in the world connected to the Internet or similar network.

Embodiments of the invention can form a substantially airtight inlet seal among the vacuum pump, inlet tube, and chamber at the sampling position by using a first pair of spring-loaded, double-lipped cups biased against opposite faces of the wheel assembly. Similarly, a embodiments of the invention can form a substantially airtight outlet seal among the compressor, outlet tube, and chamber at the transport position by using second pair of spring-loaded, double-lipped cups biased against opposite faces of the wheel assembly.

Embodiments of the invention can utilize a vacuum pump to pull ambient air through an air-sampling cartridge retained in the chamber at the sampling position, and can utilize a compressor to apply pneumatic pressure to an air-sampling cartridge retained in the chamber at the transport position thereby transporting said air-sampling cartridge through tubes to a remote destination, which can be up to several miles away. Such embodiments can utilize both the vacuum pump and compressor simultaneously to allow simultaneous sampling operation and transport operation.

Embodiments of the invention can perform both vacuum and pressurizing functions with a single compressor. Three-way ball valves, or other valves, can alternately switch air pathways between sampling operation and transport operation to allow a single compressor to perform both vacuum and pressurizing functions.

Embodiments of the invention can incorporate radiological, chemical, and/or biological detectors to analyze samples within the air-sampling cartridges before they are transported to a remote destination. Before transport, an air-sampling cartridge can be aligned with a detector at an analysis position where an air sample can be analyzed within the air-sampling cartridge while still loaded in a chamber.

Embodiments of the invention can add a pressure transducer connected to the compressor line to measure air pressure in the compressor line and connected components, such as the aligned chamber at the transport position and the outlet tube, and also connected to the vacuum line to measure air pressure in the vacuum line and connected components, such as the aligned chamber at the sampling position and the inlet tube. In such embodiments of the invention, the pressure transducer is in communication with a controller or communications board and can relay air pressure data to a remote site.

BRIEF DESCRIPTION OF THE DRAWINGS

So that the manner in which the above recited summary features of the present invention can be understood in detail, a more particular description of the invention may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

FIG. 1A is a perspective view of one embodiment of an automatic re-loading air-sampling and pneumatic transport system constructed in accordance with the teachings of the present invention with a view of a front face of a wheel assembly.

FIG. 1B is a partial perspective view of the same embodiment depicted in FIG. 1A with a view of a rear face of a wheel assembly.

FIG. 1C is a partial perspective view of the same embodiment depicted in FIG. 1A with a view of the front face of the wheel assembly and the interior of some of its chambers.

FIG. 2 is a partial perspective view of the embodiment depicted in FIG. 1A from the opposite side and with the wheel assembly removed.

FIG. 3 is a partial perspective view of the embodiment illustrated in FIG. 1A and FIG. 2 showing an exploded view of the components that comprise the front seal assembly and rear seal assembly.

DETAILED DESCRIPTION

Embodiments of the present invention now may be described more fully hereinafter with reference to the accompanying drawings, in which some, but not all, embodiments of the invention are shown. Indeed, the invention may be embodied in many different forms and should not be construed as limited to the embodiments set forth herein. Like numbers refer to like elements throughout.

Figure 1A:
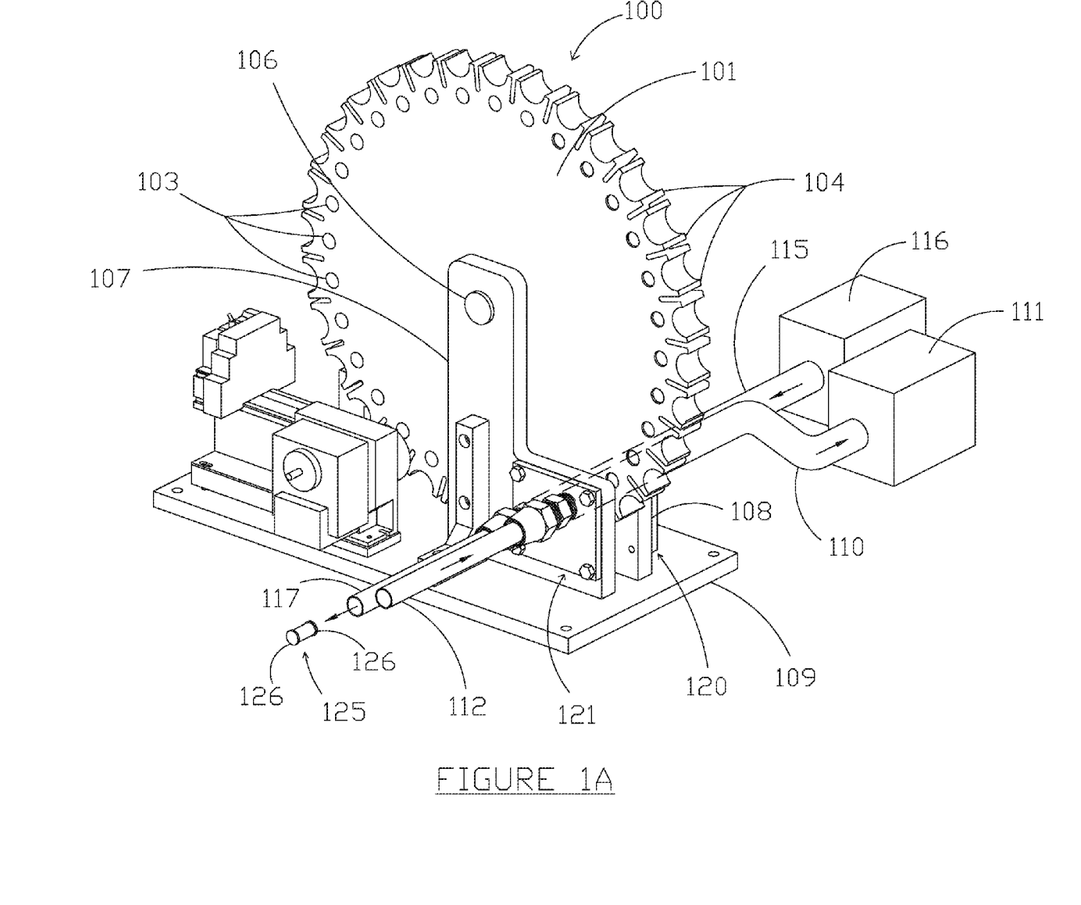

FIG. 1A is a perspective view of one embodiment of an automatic re-loading air-sampling and pneumatic transport system constructed in accordance with the teachings of the present invention with a view of a front face of a wheel assembly. In FIG. 1A, an embodiment of automatic re-loading air-sampling and pneumatic transport system 100 comprises a wheel assembly 101 composed of Teflon-like Delrin® and contains a plurality of chambers 103 comprising transverse cylindrical spaces with differently sized openings on opposite faces of the wheel assembly. The chambers 103 are arranged in a radial pattern equidistant from the center of the wheel assembly 101. The wheel assembly 101 has teeth 104 along the circumference for interaction with a rotating mechanism. In an embodiment, the depicted teeth 104 are configured to interact with a specially designed cam 202 of a Geneva drive (see FIG. 2), which rotates the wheel assembly 101 between sampling and transport operations and stops the wheel assembly 101 during sampling and transport operations. The wheel assembly 101 rotates on an axle 106 and is held in place by a front wheel mount 107 and a rear wheel mount 108 attached to a support base 109. A vacuum line 110 from the vacuum pump 111 is connected to a rear seal assembly 120 and configured to be aligned with an inlet tube 112 connected to a front seal assembly 121. A compressor line 115 from the compressor 116 is also connected to the rear seal assembly 120 and configured to be aligned with an outlet tube 117 that is also connected to the front seal assembly 121.

In an embodiment of the invention, air-sampling cartridge 125 can be a rigid hollow cylinder with a media pad 126 on at least one end. Media pad 126 can comprise any of a variety of sampling media, including fibrous, membranous, and/or perforated media, as well as an adsorbent and/or gel-based media, depending on a variety of factors, including the intended aerosol to be analyzed. Other embodiments of the invention can use solid air-sampling cartridges 125 comprising a matrix of media including fiber, such as cellulose, without a separate media pad 126. In still other embodiments of the invention, air-sampling cartridge 125 can be a rigid hollow cylinder that is filled with sampling media, including fibrous, membranous, and/or perforated solid media, as well as adsorbents and/or gel-based media.

Some embodiments of the invention can attach an end-cap to the vacuum side of air-sampling cartridge 125. An end-cap can also be optionally attached to the vacuum side of media pad 126 (or the vacuum side of air-sampling cartridge 125 if media pad 126 is not used). An end-cap could be made of material such as Mylar film and could optionally include cut flaps that open during the sampling operation to allow airflow through the sampling media and then close during the transport operation to provide resistance against pneumatic pressure supplied by the compressor 116.

Figure 1B:
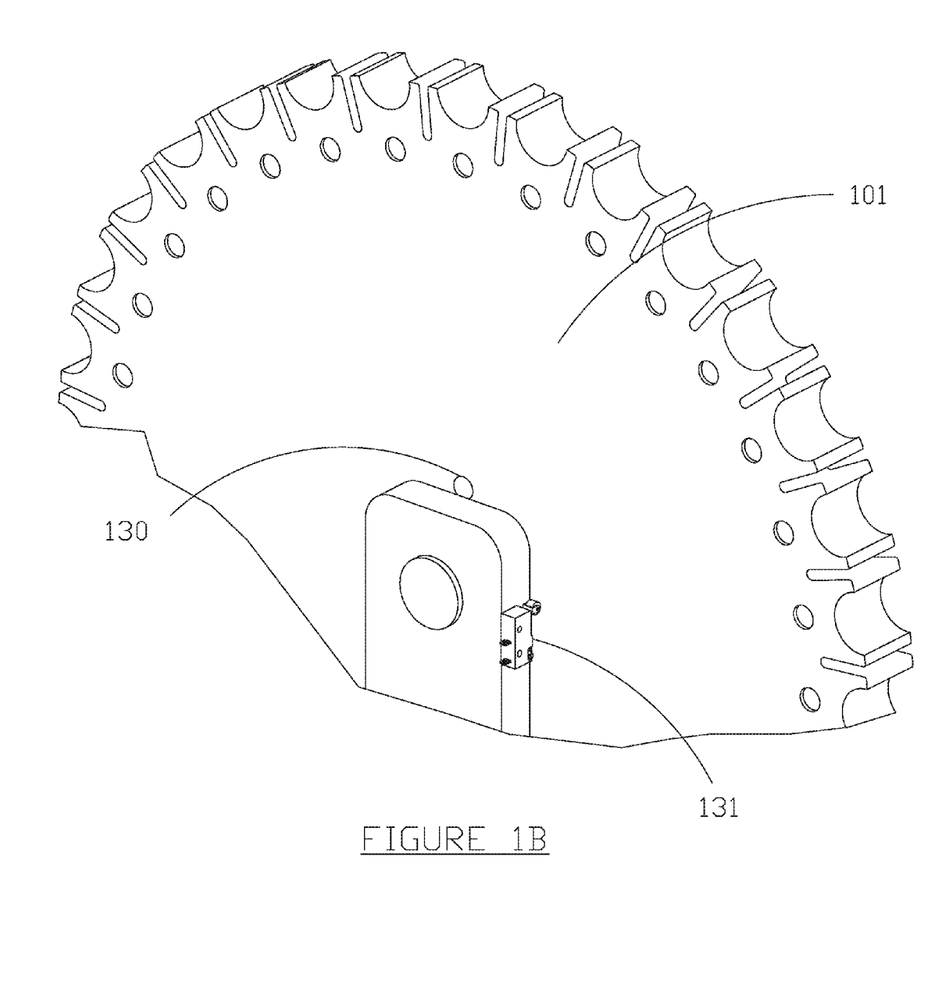

FIG. 1B is a partial perspective view of the same embodiment depicted in FIG. 1A with a view of a rear face of a wheel assembly. In FIG. 1B, the rear side of the wheel assembly 101 has at least one special cartridge marker 130 that comprises a partially drilled hole sensed by a special cartridge detector 131. The special cartridge detector 131 is in communication with a controller 611 (see FIG. 6B) that can indirectly rotate the wheel assembly 101 to a position where special cartridge marker 130 is sensed by special cartridge detector 131. When wheel assembly 101 is in this position, a specific chamber 103 associated with the special cartridge marker 130 is aligned at the sampling position. Using this technique of placing wheel assembly 101 in a known configuration, an operator can load air-sampling cartridges 125 into chambers 103 associated with the special cartridge markers 130. Then, controllers within embodiments of the invention can be programmed to rotate wheel assembly 101 into a position where a specific chamber 103 associated with a special cartridge marker 130 is aligned with the sampling position. This operation can be performed by pre-programmed instructions within a controller or on demand via remote communication.

Figure 1C:
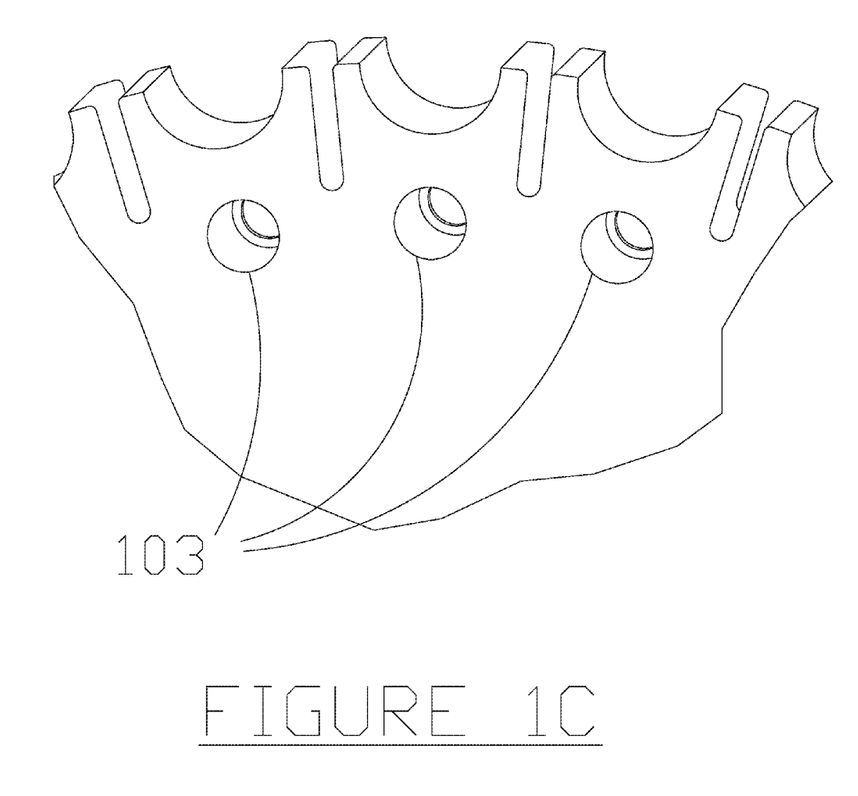

FIG. 1C is a partial perspective view of the same embodiment depicted in FIG. 1A with a view of the front face of the wheel assembly 101 and the interior of some of the chambers 103. In FIG. 1C, the openings of the chambers 103 on the front face of the wheel assembly 101 have a diameter that is equal to or greater than the diameter of the air-sampling cartridges 125. The openings of the chambers 103 on the rear face of the wheel assembly 101 have a diameter less than the diameter of the air-sampling cartridges 125. The differently sized openings allow an air-sampling cartridge 125 to be loaded through the larger opening on the front side of the wheel assembly 101 and remain retained in the wheel assembly 101 while air is drawn by the vacuum pump 111 through the smaller opening on the rear face of the wheel assembly 101 during sampling operation.

Figure 2:
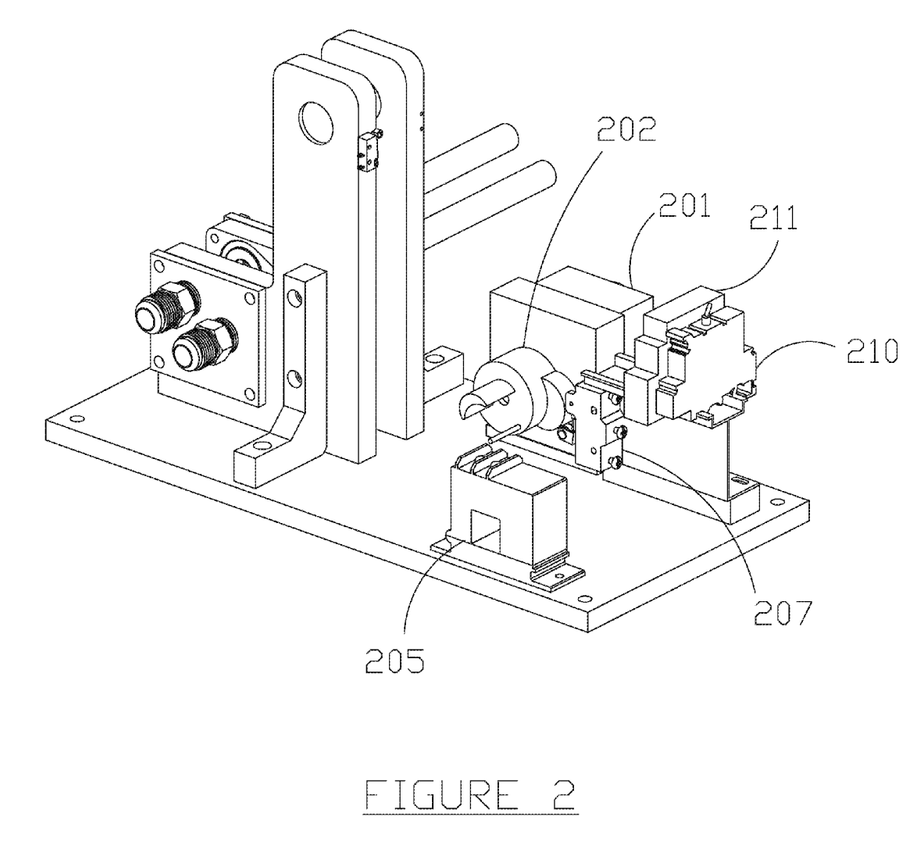

FIG. 2 is a partial perspective view of the embodiment depicted in FIG. 1A from the opposite side and with the wheel assembly removed. In FIG. 2, the Geneva drive motor 201, or other rotation mechanism, rotates a cam 202 that interacts with the wheel assembly teeth 104 in such a way that each turn of the cam 202 rotates the wheel assembly 101 to advance each chamber 103 by one position. At each stop of the cam 202, one chamber 103 is in alignment with an inlet tube 112 and vacuum line 110 at a sampling position and a second chamber 103 is aligned with an outlet tube 117 and a compressor line 115 at a transport position. In the instant embodiment, when the Geneva drive motor 201 rotates the wheel assembly 101, all chambers 103 are advanced one position such that a chamber 103 retaining an unused air-sampling cartridge 125 is advanced to the sampling position, the chamber retaining a now used air-sampling cartridge 125 in the sampling position is advanced to the transport position, and the now empty chamber 103 in the transport position is advanced beyond the transport position.

A rocker switch 207 can cut power to the on/off switch 211 when triggered by the cam 202 and thereby stop rotation of the cam 201 and consequently hold the wheel assembly 101 in position. A current sensor 205 in communication with a controller can detect which electrical circuits connected to the Geneva drive motor 201 are energized in order for the controller to reactivate the Geneva drive motor 201 through the on/off switch 211. A manual switch 210 can allow an operator to manually trigger the Geneva drive motor 201 for loading air-sampling cartridges 125 or maintenance, if necessary.

Figure 3:
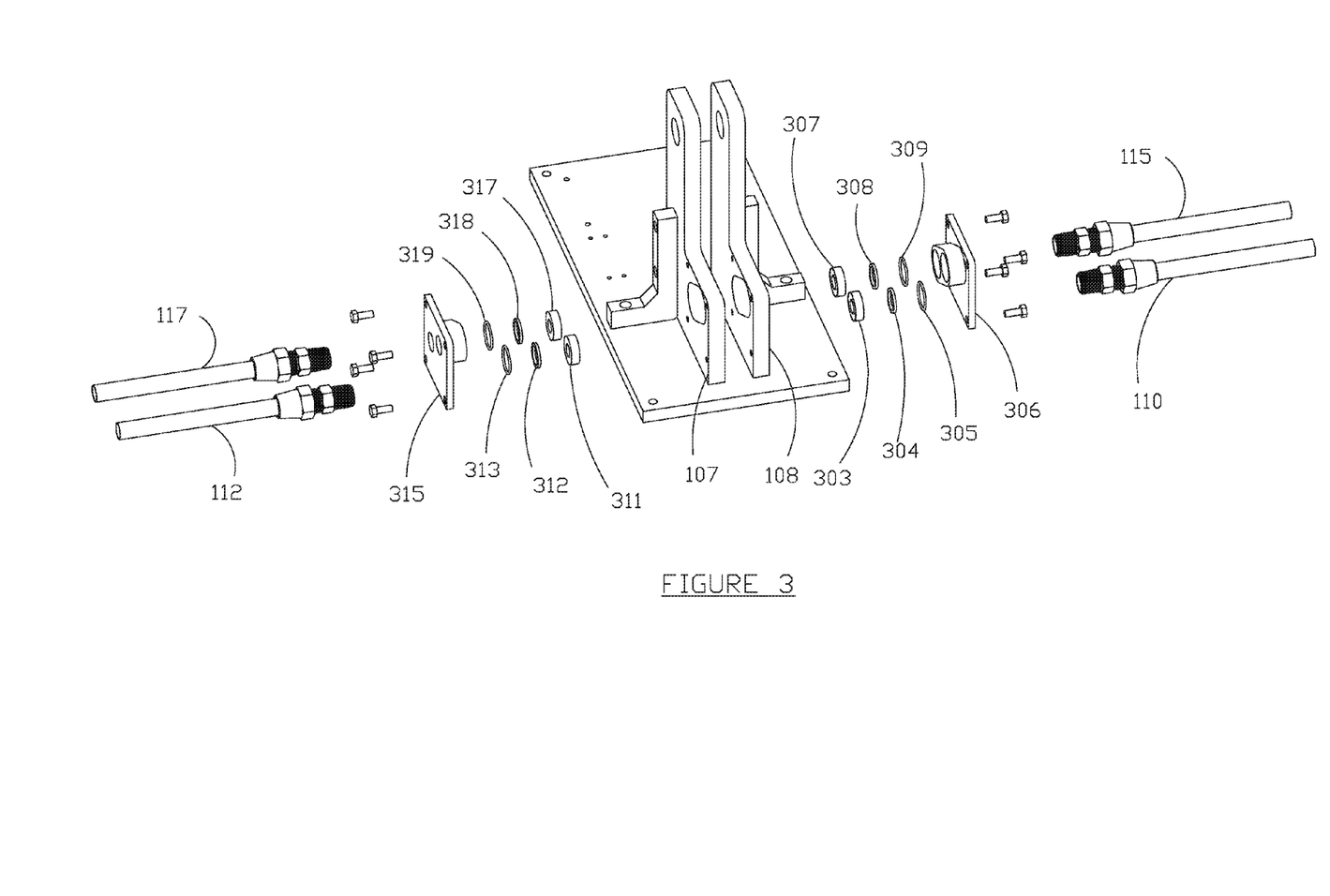

FIG. 3 is a partial perspective view of the embodiment illustrated in FIG. 1A and FIG. 2 showing an exploded view of the components that comprise the front seal assembly and rear seal assembly. In FIG. 3, the rear seal assembly 120 forms a substantially airtight seal between the vacuum line 110 and the rear face of the wheel assembly 101, while allowing free rotation of the wheel assembly 101, by biasing a double-lipped cup 303 with a wave spring washer 304 positioned between the double-lipped cup 303 and an O-ring 305 adjacent to a rear backing plate 306. The rear seal assembly 120 also forms a substantially airtight seal between the compressor line 115 and the rear face of the wheel assembly 101, while allowing free rotation of the wheel assembly 101, by biasing a double-lipped cup 307 with a wave spring washer 308 positioned between the double-lipped cup 307 and an O-ring 309 adjacent to the rear backing plate 306.

The front seal assembly 121 forms a substantially airtight seal between the inlet tube 112 and the front face of the wheel assembly 101, while allowing free rotation of the wheel assembly 101, by biasing a double-lipped cup 311 with a wave spring washer 312 positioned between the double-lipped cup 311 and an O-ring 313 adjacent to a front backing plate 315. The front seal assembly 121 also forms a substantially airtight seal between the outlet tube 117 and the front face of the wheel assembly 101, while allowing free rotation of the wheel assembly 101, by biasing a double-lipped cup 317 with a wave spring washer 318 positioned between the double-lipped cup 317 and an O-ring 319 adjacent to the front backing plate 315.

The rear backing plate 306 has a projection to retain the double-lipped cups 303, 307, wave spring washers 304, 308, and O-rings 305, 309. The front backing plate 315 has a projection to retain the double-lipped cups 311, 317, wave spring washers 312, 318, and O-rings 313, 319.

The rear wheel mount 108 has a cutaway to allow the projection of the rear backing plate 306 to pass through and approach the rear face of the wheel assembly 101. The front wheel mount 107 has a cutaway to allow the projection of the front backing plate 315 to pass through and approach the front face of the wheel assembly 101.

Figure 4:
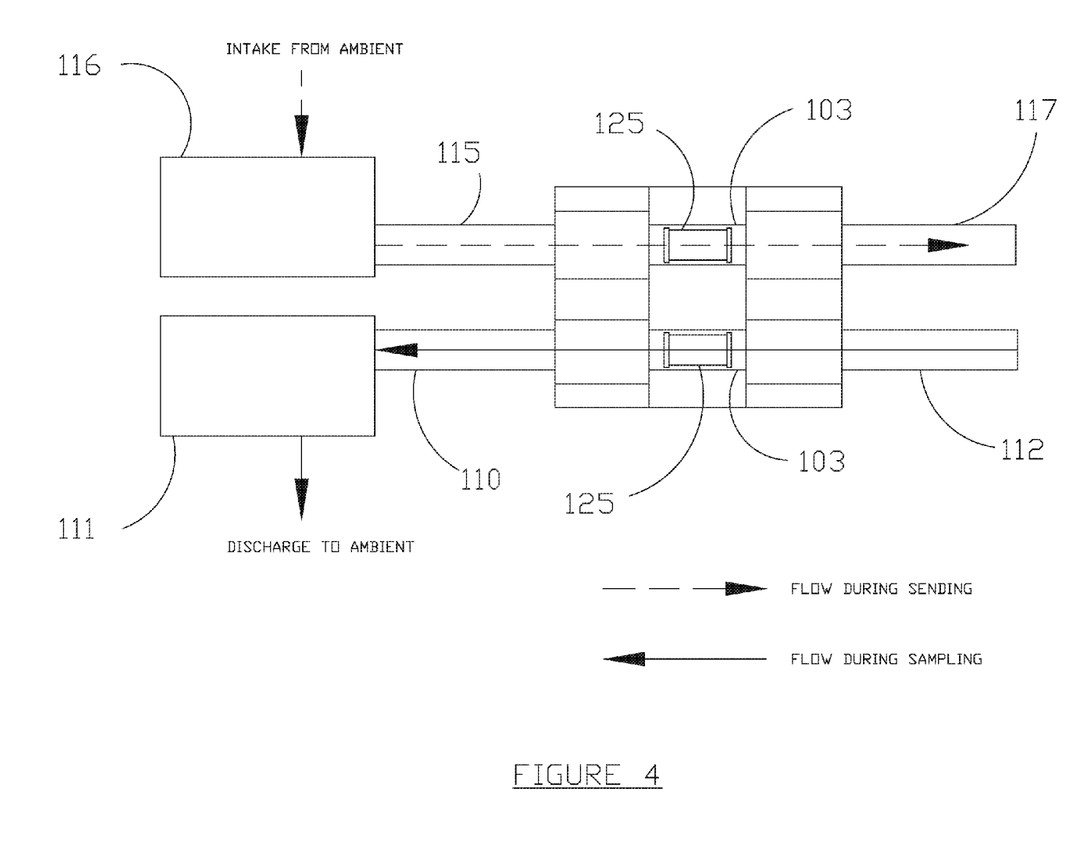
FIG. 4 is a schematic representation of the airflow pathways through an embodiment of the invention utilizing one compressor and one vacuum pump for separate sampling and transport operations.

FIG. 4 is a schematic representation of the airflow pathways through an embodiment of the invention utilizing one compressor and one vacuum pump for separate sampling and transport operations. In FIG. 4, during sampling operation, ambient air is pulled in from the inlet tube 112, through an air-sampling cartridge 125 retained in a chamber 103 at the sampling position, then through a vacuum line 110 to the vacuum pump 111, where the air is then discharged to the ambient environment. During transport operation, ambient air is pulled in at the compressor 116, which then creates pneumatic pressure in the compressor line 115 and pushes an air-sampling cartridge 125 retained in a chamber 103 at the transport position out through the outlet tube 117.

Figure 5:
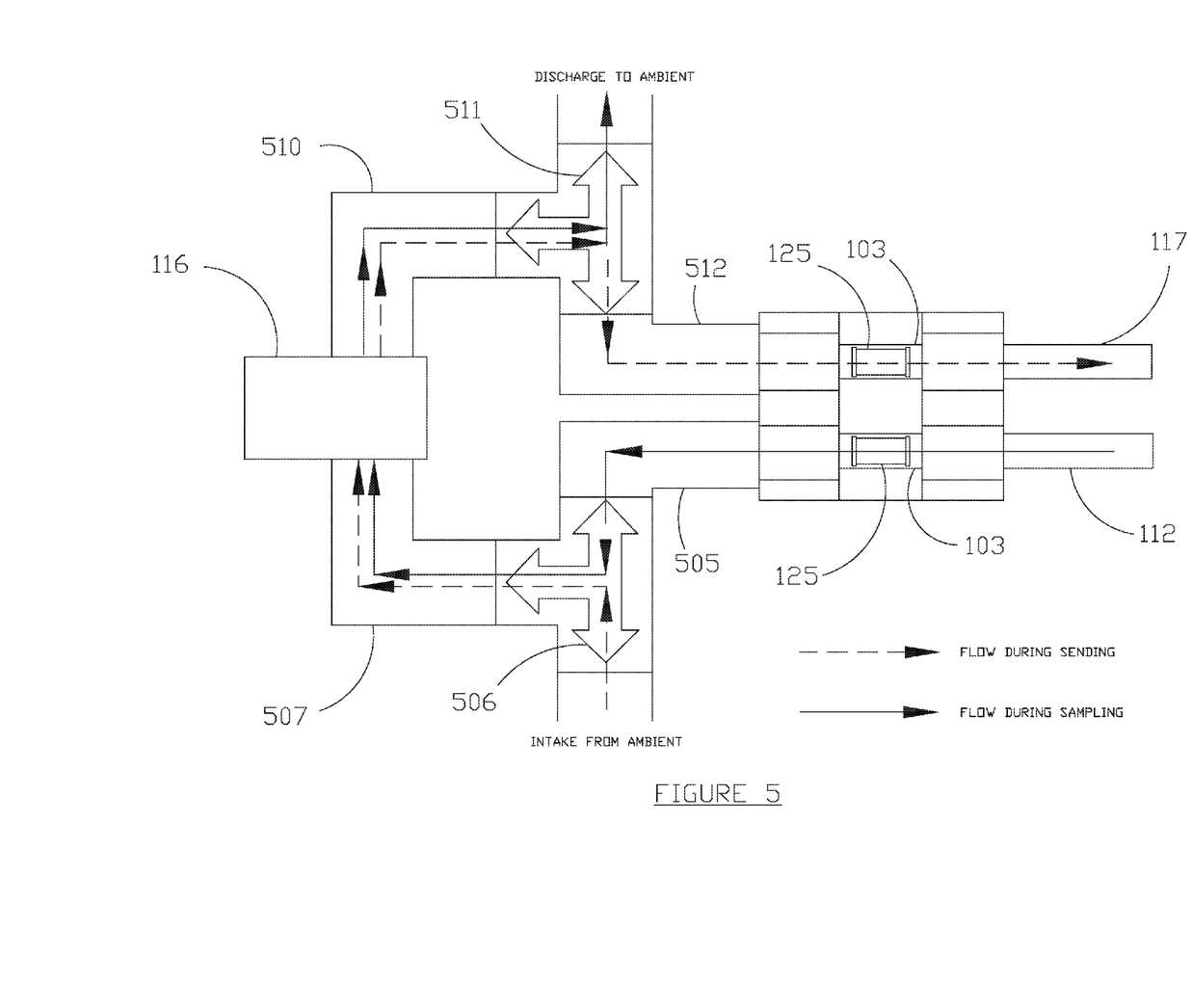
FIG. 5 is a schematic representation of the airflow pathways through an embodiment of the invention utilizing a single compressor and two three-way valves for both sampling operation and transport operation.

FIG. 5 is a schematic representation of the airflow pathways through an embodiment of the invention utilizing a single compressor and two three-way valves for both sampling operation and transport operation. In FIG. 5, during sampling operation, ambient air is pulled in from the inlet tube 112, through an air-sampling cartridge 125 retained in a chamber 103 at the sampling position, through a first vacuum line 505 connected to a first three-way valve 506 set to direct air to a second vacuum line 507 connected to a compressor 116, where it is then discharged through a first compressor line 510 connected to a second three-way valve 511 set to discharge air into the ambient environment. During transport operation, the three-way valves are switched to direct air in following way: ambient air is pulled in from the first three-way valve 506 set to receive air from the ambient environment, then though the second vacuum line 507 to the compressor 116, which creates pneumatic pressure in the first compressor line 510 connected to the second three-way valve 511 set to direct air through a second compressor line 512 and push an air-sampling cartridge 125 retained in a chamber 103 at the transport position out through the outlet tube 117 to a remote destination.

Figure 6A:
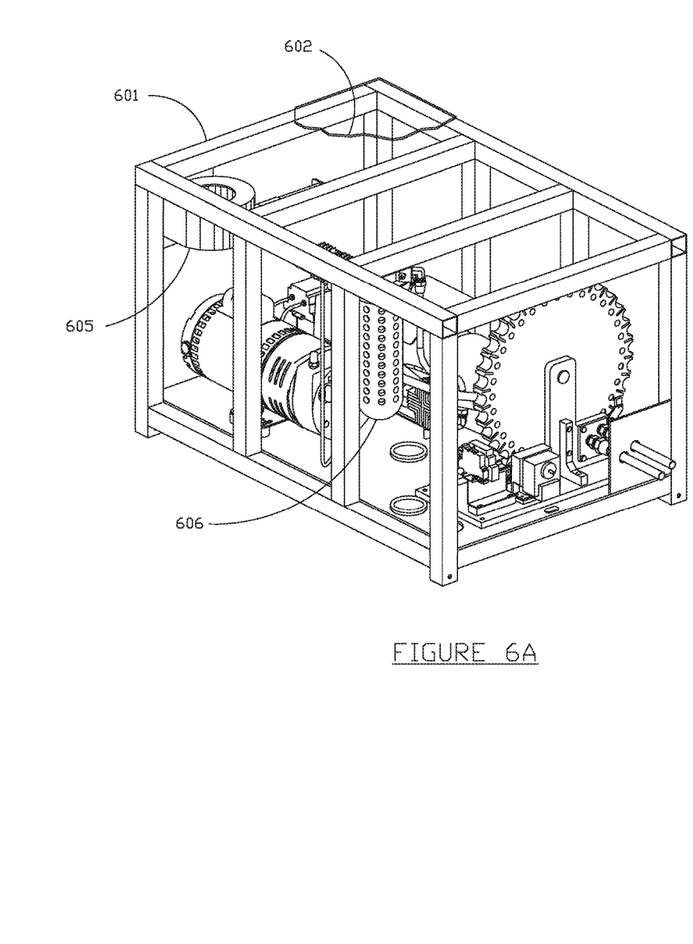
FIG. 6A is a partial perspective view of an embodiment of the invention encased within a chassis.

FIG. 6A is a partial perspective view of an embodiment of the invention encased within a chassis. In FIG. 6A, an embodiment of the invention can be housed in a chassis 601 that can be overlaid with cover plates 602. An internal fan 605 can be attached to the interior of chassis 601 to exhaust hot air. A desiccant assembly 606 can be connected between the compressor 116 and compressor line 115 to help prevent moisture accumulation in the outlet tube 117 and compressor line 115.

Figure 6B:
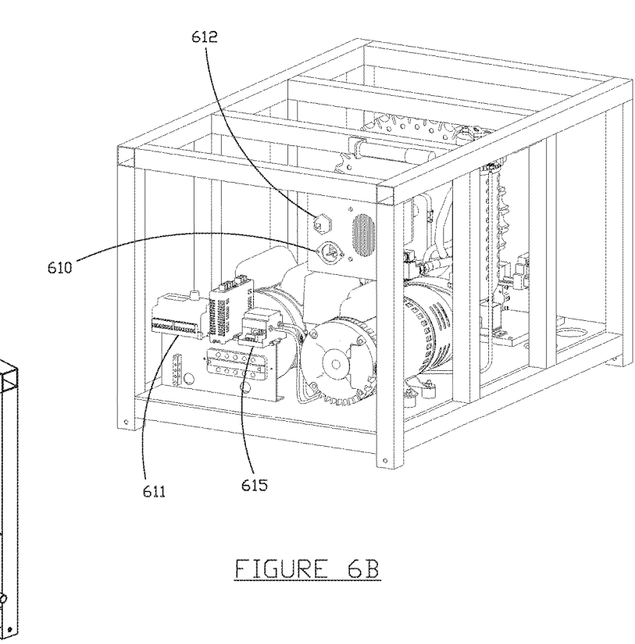
FIG. 6B is another partial perspective view of the same embodiment depicted in FIG. 6A with a view from the opposite side.

FIG. 6B is another partial perspective view of the same embodiment depicted in FIG. 6A with a view from the opposite side. In FIG. 6B, a power receptacle 610 can be attached to the chassis 601, which can distribute electricity from an external 120V power source to the vacuum pump 111, compressor 116, and controller 611 with associated communications board. A pressure transducer 615 can be connected to the compressor line 115 to measure the air pressure in the compressor line 115 and connected components, such as the aligned chamber 103 at the transport position and the outlet tube 117, and also connected to the vacuum line 110 to measure the air pressure in the vacuum line 110 and connected components, such as the aligned chamber 103 at the sampling position and the inlet tube 112. An Ethernet jack 612 that is in communication with controller 611 allows wired remote operation of the system. Alternatively, an embodiment of the invention can be equipped with a wireless communication module or chip that is in communication controller 611 and allows wireless remote operation of the system.

Figure 7:
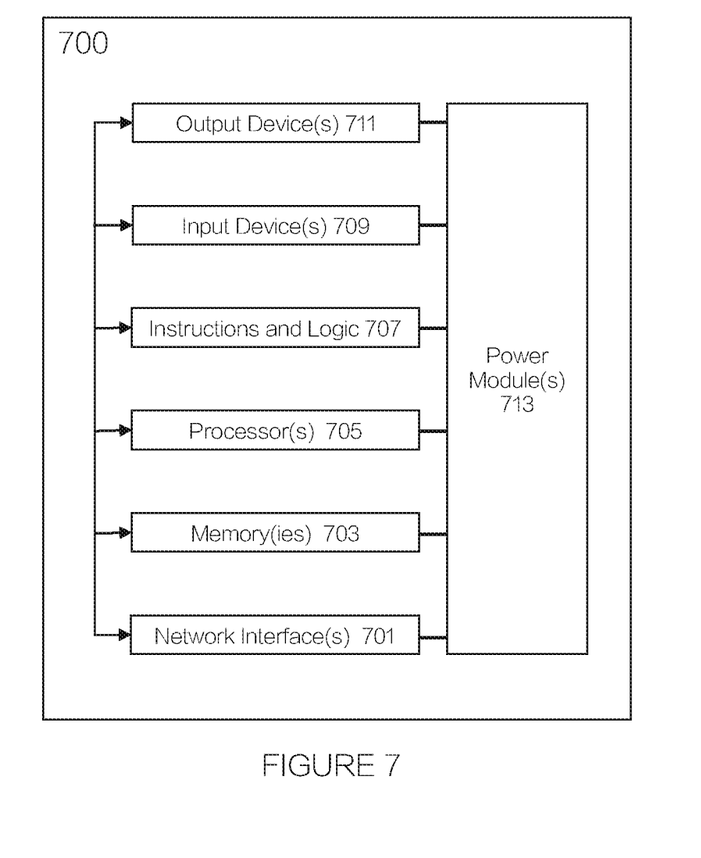
FIG. 7 is a block diagram of an exemplary embodiment of a computing device 700 that is configured to control the operation of various embodiments of the invention.

FIG. 7 is a block diagram of an exemplary embodiment of a computing device 700 that is configured to control the operation of various embodiments of the invention. In certain operative embodiments, computing device 700 is the controller 611 of FIG. 6B. Computing device 700 may comprise any device known in the art to be capable of processing data and/or information and also capable of being installed on or embedded within an embodiment of automatic re-loading air-sampling and pneumatic transport system 100. Accordingly, computing device 700 may comprise a general purpose and/or special purpose computer, including a microprocessor or microcontroller, a personal computer, workstation, server, minicomputer, microcomputer, computer terminal, laptop, tablet computer (such as an iPad), mobile terminal, smart phone (such as an iPhone, Android device, or BlackBerry) or the like. In general, any device on which resides a finite state machine capable of implementing at least a portion of a control operation, method, Application Programmer's Interface ("API"), communications interface, and/or user interface described herein may be used as a computing device. Computing device 700 may comprise any of numerous components, including one or more network interface(s) 701, one or more memory(ies) 703, one or more processor(s) 705, program instructions and logic 707, one or more input device(s) 709, one or more output device(s) 711, and one or more power module(s) 713.

Network interface(s) 701 may comprise any device, system, or subsystem or component that is capable of coupling an information device to a network and/or transmitting or receiving information. For example, a network interface can comprise a telephone, cellular phone, cellular modem, telephone data modem, fax modem, wireless transceiver, RF transceiver, Bluetooth transceiver, WiFi transceiver, wireless broadband transceiver (WiMAX), Ethernet circuit, cable modem, digital subscriber line interface, bridge, hub, router, or other similar capability.

Memory(ies) 703 can be any type of apparatus known in the art that is capable of storing analog or digital information such as instructions and/or data. Examples include a non-volatile or read only memory ("ROM"), volatile or random access memory ("RAM"), flash memory, various types of magnetic memory media, and the like. Memory(ies) 703 can be coupled to one or more processor(s) 705 and can store instructions and logic 707 adapted to be executed by one or more processor(s) 705, as according to any of the embodiments disclosed herein.

Processor(s) 705 may comprise one or more devices for executing machine-readable instructions that perform one or more predetermined tasks. Processor(s) 705 can comprise any one or a combination of hardware, firmware, and/or software. In general, processor(s) 705 can utilize mechanical, pneumatic, hydraulic, electrical, magnetic, optical, informational, chemical, and/or biological principles, signals, and/or inputs to perform tasks. In certain embodiments, processor(s) 705 can receive information from input device(s) 709. In certain embodiments, processor(s) 705 can act upon information, including received information, by manipulating, analyzing, modifying, converting, transmitting the information for use by an executable procedure and/or an information device, and/or routing the information to output device(s) 711. Processor(s) 705 can function as a central processing unit, local controller, remote controller, parallel controller, and/or distributed controller, etc. Processor(s) 705 can include a general-purpose device, such as a microcontroller and/or a microprocessor. In certain embodiments, processor(s) 705 can be a dedicated special purpose device, such as an Application Specific Integrated Circuit ("ASIC") or a Field Programmable Gate Array ("FPGA"). Processor(s) 705 can also be an integrated circuit that has been designed to implement in hardware and/or firmware at least a part of an embodiment disclosed herein. Processor(s) 705 can also include a hardware electronic logic circuit such as a discrete element circuit, and/or a programmable logic device such as a Programmable Logic Controller ("PLC") or the like.

Instructions and logic 707 may comprise directions adapted to cause a machine, such as computing device 700, to perform one or more particular activities, operations, or functions. The directions, which can sometimes form an entity called a "kernel", "operating system", "program", "application", "utility", "subroutine", "script", "macro", "file", "project", "module", "library", "class", "object", or "Application Programming Interface," etc., can be embodied as machine code, source code, object code, compiled code, assembled code, interpretable code, and/or executable code, etc., in hardware, firmware, and/or software. Instructions and logic 707 may reside in processor(s) 705, in memory(ies) 703, or in another specialized device(s) or component(s). Instructions and logic 707 may also be embedded in an external computer-readable storage medium or device, which when loaded into computing device 700 is able to carry out the different control instructions, steps, and methods described herein.

Input device(s) 709 may comprise any traditional input device known in the art, such as a button, dial, or switch, and may also include any sensory-oriented input device known in the art, such as an audio, visual, haptic, olfactory, and/or taste-oriented device, including, for example, a keyboard, keypad, mouse, trackball, joystick, gamepad, wheel, touchpad, touch panel, pointing device, microphone, speaker, video camera, camera, scanner, printer, haptic device, vibrator, tactile simulator, and/or tactile pad, potentially including a port to which an input device can be attached or connected. Input device(s) 709 may also comprise any sensor known in the art that can measure physical/spatial parameters, including vibrations, acceleration, and direction of motion.

Output device(s) 711 may comprise any output device known in the art, such as, for example, a monitor, display, projector, overhead display, printer, switch, relay, solenoid, light-producing device, audio or sound-producing device, or vibrator, potentially including a port to which output device(s) 711 can be attached or connected.

Computing device 700 may be used, accessed, programmed, controlled, manipulated, or directed through a user interface. The user interface may comprise any means for rendering information to a user and/or requesting information from the user. A user interface includes at least one of textual, graphical, audio, video, animation, and/or haptic elements. A textual element can be provided, for example, by a printer, monitor, display, projector, etc. A graphical element can be provided, for example, via a monitor, display, projector, and/or visual indication device, such as a light, flag, beacon, etc. An audio element can be provided, for example, via a speaker, microphone, and/or other sound generating and/or receiving device. A video element or animation element can be provided, for example, via a monitor, display, projector, and/or other visual device. A haptic element can be provided, for example, via a very low frequency speaker, vibrator, tactile stimulator, tactile pad, simulator, keyboard, keypad, mouse, trackball, joystick, gamepad, wheel, touchpad, touch panel, pointing device, and/or other haptic device, etc. A user interface can include one or more textual elements such as, for example, one or more letters, number, symbols, etc. A user interface can include one or more graphical elements such as, for example, an image, photograph, drawing, icon, window, title bar, panel, sheet, tab, drawer, matrix, table, form, calendar, outline view, frame, dialog box, static text, text box, list, pick list, pop-up list, pull-down list, menu, tool bar, dock, check box, radio button, hyperlink, browser, button, control, palette, preview panel, color wheel, dial, slider, scroll bar, cursor, status bar, stepper, and/or progress indicator, etc. A textual and/or graphical element can be used for selecting, programming, adjusting, changing, specifying, etc. an appearance, background color, background style, border style, border thickness, foreground color, font, font style, font size, alignment, line spacing, indent, maximum data length, validation, query, cursor type, pointer type, autosizing, position, and/or dimension, etc. A user interface can include one or more audio elements such as, for example, a volume control, pitch control, speed control, voice selector, and/or one or more elements for controlling audio play, speed, pause, fast forward, reverse, etc. A user interface can include one or more video elements such as, for example, elements controlling video play, speed, pause, fast forward, reverse, zoom-in, zoom-out, rotate, and/or tilt, etc. A user interface can include one or more animation elements such as, for example, elements controlling animation play, pause, fast forward, reverse, zoom-in, zoom-out, rotate, tilt, color, intensity, speed, frequency, appearance, etc. A user interface can include one or more haptic elements such as, for example, elements utilizing tactile stimulus, force, pressure, vibration, motion, displacement, temperature, etc.

Power module(s) 713 may comprise one or more devices for providing electrical power to various the components of computing device 700. Power module(s) 713 may include one or more battery cells or other power supplies, any number of which can be electrically connected together. Some or all of the battery cells may be rechargeable. Power module(s) 713 may also include a power input to receive input power from a power source, and a power output to provide output power to another device, including another power module 713.

Embodiments of the invention can utilize computing device 700 to provide autonomous or manual-assisted control over various operations of automatic re-loading air-sampling and pneumatic transport system 100. Said operation can include, but is not limited to: receiving electronic communications and commands via Ethernet jack 612, controlling Geneva drive motor 201, activating and terminating operation of vacuum pump 111, activating and terminating operation of compressor 116, and three-way valves 506 and 511, as explained above.

In addition to the illustrated embodiments, one of ordinary skill in the art will understand that an alternative embodiment of the invention can include a detection system such that air samples can be analyzed after collection but prior to transport, that is, while an air-sampling cartridge 125 is still retained in a chamber 103 of the wheel assembly 101. Such a detection system can be located between the sampling and transport positions, but may also be located at another position along the wheel assembly 101. Such alternative embodiments of the invention can include detectors to detect specific chemical compounds, biological components, and/or radiological emissions from an air sample.

The foregoing disclosure has been set forth merely to illustrate the invention and is not intended to be limiting. It will be appreciated that modifications, variations and additional embodiments are covered by the above teachings and within the purview of the appended claims without departing from the spirit and intended scope of the invention. Other logic may also be provided as part of the exemplary embodiments but are left out here so as not to obfuscate the present invention. Since modifications of the disclosed embodiments incorporating the spirit and substance of the invention may occur to persons skilled in the art, the invention should be construed to include everything within the scope of the appended claims and equivalents thereof.

The invention claimed is:

1. A method for sampling air, comprising:
   (a) pulling a partial vacuum on a vacuum line to draw ambient air through an air inlet tube and a first air-sampling cartridge retained in a first chamber of a cartridge magazine, where the cartridge magazine has a plurality of chambers, where the vacuum line is aligned with the first chamber on one side of the cartridge magazine, where the air inlet tube is aligned with the first chamber on the opposite side of the cartridge magazine, and where the partial vacuum causes an aerosol sample from the ambient air to be deposited onto sampling media of the first air-sampling cartridge;
   (b) advancing the cartridge magazine to move the first chamber out of alignment with the air inlet tube and into alignment with an air outlet tube, and to move a second chamber of the cartridge magazine into alignment with the air inlet tube; and
   (c) applying pneumatic pressure to transport the first air-sampling cartridge out of the first chamber through the air outlet tube to a remote destination.

2. The method of claim 1, wherein a second air-sampling cartridge is retained in the second chamber.

3. The method of claim 1, wherein the cartridge magazine is a wheel assembly and the plurality of chambers are arranged in a radial pattern.

4. The method of claim 3, further comprising:
   advancing the wheel assembly using a Geneva drive mechanism.

5. The method of claim 1, further comprising:
   triggering any of the steps (a), (b), or (c) from instructions issued by a local controller.

6. The method of claim 1, further comprising:
   triggering any of the steps (a), (b), or (c) from instructions issued by a remote controller.

7. The method of claim 1, further comprising:
   advancing the cartridge magazine to move the first chamber into alignment with a detector at an analysis position.

8. The method of claim 7, further comprising:
   analyzing the aerosol sample at the analysis position to detect the presence of a radiological element.

9. The method of claim 7, further comprising:
   analyzing the aerosol sample at the analysis position to detect the presence of a chemical element.

10. The method of claim 7, further comprising:
    analyzing the aerosol sample at the analysis position to detect the presence of a biological element.

11. The method of claim 1, further comprising:
    measuring the air pressure in the outlet tube via a pressure transducer.

12. The method of claim 11, further comprising:
    transmitting data about the measured air pressure to a remote location.

13. The method of claim 1, further comprising:
    measuring the air pressure in the vacuum line via a pressure transducer.

14. The method of claim 13, further comprising:
    transmitting data about the measured air pressure to a remote location.

* * * * *